United States Patent
Ioannides et al.

(10) Patent No.: US 11,813,329 B2
(45) Date of Patent: Nov. 14, 2023

(54) METHOD AND COMPOSITION FOR TREATING CANCER OR SKIN LESION USING A VACCINE

(71) Applicant: HPVVAX, LLC, Port St. Lucie, FL (US)

(72) Inventors: Tim Ioannides, Vero Beach, FL (US); Evangelos V. Badiavas, Miami, FL (US)

(73) Assignee: HPVVAX, LLC, Port St. Lucie, FL (US)

( * ) Notice: Subject to any disclaimer, the term of this patent is extended or adjusted under 35 U.S.C. 154(b) by 274 days.

(21) Appl. No.: 17/068,087

(22) Filed: Oct. 12, 2020

(65) Prior Publication Data

US 2021/0030872 A1    Feb. 4, 2021

Related U.S. Application Data

(63) Continuation-in-part of application No. 15/442,281, filed on Feb. 24, 2017, now Pat. No. 10,799,574, which is a continuation-in-part of application No. 14/921,648, filed on Oct. 23, 2015, now Pat. No. 10,238,729.

(60) Provisional application No. 62/455,434, filed on Feb. 6, 2017, provisional application No. 62/444,576, filed on Jan. 10, 2017, provisional application No. 62/338,183, filed on May 18, 2016, provisional application No. 62/328,487, filed on Apr. 27, 2016, provisional application No. 62/300,785, filed on Feb. 27, 2016, provisional application No. 62/068,332, filed on Oct. 24, 2014.

(51) Int. Cl.
  *A61K 39/42* (2006.01)
  *A61K 35/00* (2006.01)
  *A61K 31/506* (2006.01)
  *A61P 35/00* (2006.01)
  A61K 39/00 (2006.01)

(52) U.S. Cl.
  CPC ............ *A61K 39/42* (2013.01); *A61K 31/506* (2013.01); *A61P 35/00* (2018.01); *A61K 2039/585* (2013.01); *A61K 2039/70* (2013.01); *A61K 2039/876* (2018.08)

(58) Field of Classification Search
  None
  See application file for complete search history.

(56) References Cited

U.S. PATENT DOCUMENTS

2020/0113996 A1* 4/2020 Wang .................. A61K 39/12
2022/0125839 A1* 4/2022 Sarnaik .............. A61K 31/506

OTHER PUBLICATIONS

Cohen et al. Novel Therapeutics for Recurrent Cervical Cancer: Moving Towards Personalized Therapy. Drugs (2020) 80:217-227.*
Siddiqui et al. Human Papillomavirus Quadrivalent (types 6, 11, 16, 18) Recombinant Vaccine (Gardasil®). Drugs 2006; 66 (9): 1263-1271.*

* cited by examiner

*Primary Examiner* — Nianxiang Zou
(74) *Attorney, Agent, or Firm* — Ted Whitlock Registered Patent Attorney, PA

(57) ABSTRACT

A method for treating or reducing the incidence of recurrence of cancer, benign tumors, or HPV-associated lesions, including skin cancer, and particularly squamous cell carcinoma (SCC and basal-cell carcinoma, by administering one or more doses of HPV recombinant vaccine to a patient.

19 Claims, No Drawings

METHOD AND COMPOSITION FOR TREATING CANCER OR SKIN LESION USING A VACCINE

CROSS-REFERENCE TO RELATED APPLICATIONS

This application is a continuation-in-part (CIP) of pending U.S. patent application Ser. No. 15/442,281, filed Feb. 24, 2017, issuing Oct. 13, 2020 as U.S. Pat. No. 10,799,574, and claiming the benefit of U.S. Provisional Appl. Ser. No. 62/455,434, filed Feb. 6, 2017; 62/444,576, filed Jan. 10, 2017; 62/338,183, filed May 18, 2016; 62/328,487 filed Apr. 27, 2016; and 62/300,785, filed Feb. 27, 2016, and which is a CIP of U.S. patent application Ser. No. 14/921,648, filed Oct. 23, 2015 now U.S. Pat. No. 10,238,729, and claiming the benefit of U.S. Provisional Application Ser. No. 62/068,332, filed Oct. 24, 2014, each and all of which are incorporated by reference in their entirety.

FIELD OF THE INVENTION

The invention relates to treating cancer, including skin cancer or benign or malignant tumor and, more particularly, to a composition and method for treatment, or reducing the incidence of recurrence, of cancer or tumors comprising administration of a vaccine, including local administration of a composition comprising the vaccine as a therapeutic agent, and further including a conventional human papillomavirus (HPV) vaccine as a first active therapeutic agent in combination with a second active therapeutic agent, administered concomitantly or as a fixed-dose combination composition.

BACKGROUND OF THE INVENTION

Skin cancer consists of three main types, namely, basal-cell carcinoma (BCC), squamous cell carcinoma (SCC) and melanoma, and is the most common form of cancer globally. Understandably, there have been ongoing studies for many years searching for effective methods to treat, and possibly cure, these types of skin cancer.

It is generally accepted that human papillomavirus (HPV) is associated with causing certain types of skin cancer, particularly squamous cell carcinoma (SCC). HPV is a DNA virus that can infect certain types of tissues in humans. There are upwards of thirty subtypes of HPV and some of these subtypes have been associated with cervical cancer, including HPV16 and HPV18. HPV is not known to be a cause or to be associated with basal cell carcinoma (BCC) or melanoma.

Vaccines have been developed and shown to prevent cervical cancer in women and other conditions caused by or associated with HPV infection. GARDASIL® is a commercially available vaccine having activity against HPV (types 6, 11, 16, and 18).

GARDASIL® 9 is another commercially available vaccine marketed for prevention of HPV (types 16, 18, 31, 33, 45, 52, and 58). GARDASIL® is indicated for use in girls and boys from ages 9-26; GARDASIL® 9 is also indicated for use in girls from ages 9-26, and in boys from ages 9-15.

Other vaccines have been produced, as well, for treating subtypes of HPV, particularly HPV16 and HPV18. GARDASIL® and other known vaccines administered prophylactically, to prevent certain HPV infections and associated cancers, are referred to herein as "preventive vaccines." These preventive vaccines are typically administered for systemic action, being injected into a patient subcutaneously or intramuscularly (e.g., deltoid), remote from any particular target, such as the cervix. Moreover, they are generally accepted to be effective prior to exposure to HPV and are not commonly known to be effective for treatment after exposure to, or infection with, HPV.

Other preventive vaccines include, for example, an improved vaccine composition as described in Chinese Pat App. No. 101890160 (CN'160) comprising certain L1 proteins of HPV (as in GARDASIL®), and additional HPV-specific components. Preventive vaccines comprising HPV-type 16 and 18 proteins are also suggested to provide cross-protection against other HPV types, as described in US Pub. No. 2005/0287161.

Vaccines used for treatment (referred to herein as "therapeutic vaccines") are described. However, these therapeutic vaccines require more than viral-specific components, such as HPV L1 proteins that comprise the commercially available preventive vaccines, such as GARDASIL®.

US Pub. No. 2007/0218074 describes the use of a vaccine composition comprising host-cell peptides from an HPV-infected cell. The host-cell peptides, e.g., the early antigens, E6 or E7, that present on the surface of cells infected with HPV, are fragments of host-cell proteins. The criticality of the polypeptides E6 or E7 in a vaccine used in treating certain cancer types is described in *Development of HPV vaccines for HPV-associated head and neck squamous cell Carcinoma*, Devaraj, et al., Crit Rev Oral Biol Med. 2003; 14(5):345-62. Another vaccine which includes a host-cell protein (BAX) is described in U.S. Pat. No. 8,399,610.

Yet another vaccine composition comprising other or additional antigens in combination with HPV-16 peptides, is a vaccine composition described in US Pub. No. 2011/0070252 which additionally requires Trojan antigen.

US Pub. No. 2011/0110979 (US '979) and US Pub. No. 2012/0288538 (US '538) disclose therapeutic use of an HPV vaccine comprising E6 or E7 polypeptides (peptide fragments from host cells infected with HPV). US '538 describes that E6 and E7 are crucial to induce transformation into HPV-infected cells, and states that a vaccine composition which does not include E6 or E7 would not be expected to work on cells that do not have E6 or E7, i.e., cells such as BCC that are not infected with HPV. The method described in the US'979 publication additionally requires an immunostimulant or adjuvant.

Although the US '979 and US '538 publications describe the use of therapeutic vaccines against skin cancers, such as SCC or epithelial SCC, they do not describe use of the vaccine against other skin cancers, such as BCC or melanoma, likely based on the understanding that BCC and melanoma are not associated with HPV infection.

New immunotherapy drugs for cancer have been a breakthrough for many cancers but there have been several failures over time. Among the newer drugs are Immune Checkpoint Inhibitors (PD-1, PD-L1, and CTLA-4 inhibitors) and CAR T-cells.

Immune Checkpoint Inhibitors have been used for solid tumors but only one, cemiplimab, that has been approved for advanced squamous cell carcinoma. Patients with complex skin squamous cell carcinomas, such as dystrophic epidermolysis bullosa patients, appear not to respond as well to Immune Checkpoint Inhibitors (cemiplimab) which appears at least at some level due to immune based dysfunction.

CAR T-cells have not performed well with solid tumors. Among the shortcomings of these therapies are that they block limited (often single) pathways. Combination of immunotherapies have produced better results, but the benefits are limited. This is due to inhibition of limited pathways. With limited pathways blocked, treated cancers have also been shown to no longer be resistant to these pathways, finding other ways to survive.

The limitations and disadvantages of the above uses of vaccines can be overcome by the use of a composition or method in accordance with the subject invention. There is a need in the medical and health fields for safe and efficacious cancer treatments, including skin cancers or cancers that are typically not associated with HPV infection, which are convenient for the patient as well as the health practitioner.

An alternative approach to boosting these therapies, such as the use of these new immunotherapies in combination with a vaccine, which is inhibitory on multiple levels, is a novel and needed advancement to the medical field.

SUMMARY OF THE INVENTION

The subject invention concerns a method for treating a patient having skin cancer, benign or malignant tumor, whether or not associated with or related to human papilloma virus (HPV) infection, or other skin lesion, said method comprising the steps of:

administering to a patient having or in need of treatment of a tumor, cancer or other skin lesion, a therapeutically effective dose of a commercially available HPV vaccine. The vaccine can be administered directly to the cancer or lesion, either by direct application onto (topical) the tumor or lesion, or by direct injection into the tumor or lesion. Alternatively, the vaccine can be administered for therapeutic use by systemic injection. A method of treatment according to the subject invention can also include any combination of topical application, direct or systemic injection. A therapeutically effective dose can be a conventional, approved dose of the vaccine per its label indication.

In one embodiment, the method can comprise:

a) administering to a patient 27 years of age or older or a patient previously not immunized with an HPV vaccine, a first dose of an HPV vaccine which is free of host-cell peptide, polypeptide, or protein or a degradant product thereof;

b) administering to the patient a second dose of the HPV vaccine about one month to about three months after the first administration; and c) optionally, administering to the patient a third dose of the HPV vaccine about five months to about seven months after the first dose.

Following the initial, conventional administration of the vaccine according to step a), above, the second or third administrations according to steps b) and c), above, can be by injection, or can be by topical administration of a composition comprising the vaccine. Alternatively, the second or third administrations of steps b) or c) can include both injection and by topical administration.

In one embodiment, the second dose of HPV vaccine is administered about two months after administering the first dose and the third dose of HPV vaccine is administered about six months after administering the first dose.

The HPV vaccine can be selected from HPV quadrivalent (types 6, 11, 16, and 18) recombinant vaccine comprising HPV L1 proteins and HPV multivalent (types 16, 18, 31, 33, 45, 52, and 58) recombinant vaccine comprising HPV L1 proteins, and preferably is free or substantially free of host-cell early antigen, e.g., E6 or E7.

In one preferred embodiment, the method does not comprise or is without administering an additional or other immunostimulant or adjuvant.

In one preferred embodiment, the method comprises administering an additional or other immunomodulatory agent, such as an immunostimulant or adjuvant.

By carrying out the method, the size of the cancer or HPV-related lesion can be substantially reduced, or completely eliminated. In addition, the incidence of recurrence of the cancer or HPV-related lesion can be reduced. The method can be effective in treating or reducing the incidence of recurrence of a cancer, benign tumor, or HPV-related lesion such as squamous cell carcinoma, basal cell carcinoma, melanoma, verruca vulgaris, or condyloma accuminata.

In one embodiment, the method can comprise a single dose of the vaccine. For example, a single dose of the vaccine can be administered topically, or by injection directly into a tumor or systemically to reduce the size or eliminate the tumor. A physician or healthcare professional can administer a second or subsequent dose, as needed or as determined by the physician or healthcare professional.

In one embodiment, the patient in need of treatment can be a person previously immunized with the vaccine. In another embodiment, the patient in need of treatment can be a person that has not been previously immunized with the vaccine.

Each dose of HPV vaccine administered in the above method steps is preferably about 0.5 ml, and is more preferably 0.5 ml.

The method can further comprise establishing a positive diagnosis of cancer, benign tumor, or HPV infection prior to administering the first dose of HPV vaccine.

An alternative embodiment of the method according to the subject invention comprises treating a patient having cancer, benign tumor, or a human papilloma virus-related (HPV-related) lesion, wherein the method comprises administering a dose of an HPV vaccine directly to the cancer, tumor, or lesion or an area immediately surrounding the tumor or lesion.

This alternative embodiment of the method according to the subject invention can further comprise the steps of:

administering a second dose of the HPV vaccine directly to the tumor or lesion or an area immediately surrounding the tumor or lesion about one month to about three months after administering the first dose; and optionally, administering a third dose of the HPV vaccine directly to the tumor or lesion or an area immediately surrounding the tumor or lesion about five months to about seven months after administering the first dose.

These direct second or third administrations of a composition comprising the vaccine can be topical applications, or can be by injection into the lesion.

In this alternative embodiment of the subject method, the second dose of HPV vaccine can be administered about two months after administering the first dose and the third dose of HPV vaccine can be administered about six months after administering the first dose.

By carrying out the alternative embodiment of the method according to the subject invention, the size of the cancer, tumor, or HPV-related lesion can be substantially reduced or completely eliminated. In addition, the incidence of recurrence of the cancer, tumor, or HPV-related lesion can be reduced.

The preferred dose of each subsequent administration of HPV vaccine, if any, is 0.5 ml.

The method according to any embodiment of the invention can be used for treating cancer, benign tumor, or HPV-related lesion, including, but not limited to, a benign tumor associated or unassociated with HPV infection, squamous cell carcinoma, basal cell carcinoma, melanoma, verruca vulgaris, and condyloma accuminata.

The method can further comprise establishing a positive diagnosis of cancer, benign tumor, or HPV infection prior to administering the first dose of HPV vaccine.

In one preferred embodiment, the direct or local administration of the vaccine is administered by injection, and more preferably the method does not comprise administering an additional or other immunostimulant or adjuvant, with, during or following the administration of the vaccine.

Alternatively, the subject method can comprise administering an additional or other immunomodulatory agent, e.g., and immunostimulant or adjuvant, with, during or following the administration of the vaccine.

Yet another embodiment of the invention includes a composition comprising, or a method of cancer treatment using, in combination, a first active agent which is an HPV vaccine and a second active agent which is an immunotherapy cancer drug, e.g., an Immune Checkpoint Inhibitors such as PD-1, PD-L1, or CTLA-4 inhibitors, or CAR T-cells.

In another preferred embodiment, the vaccine can be formulated for topical administration and applied directly to the lesion in the form of a topical solution or suspension, such as a liquid or spray, gel, cream, salve, ointment, foam or mousse, or the like.

The subject invention can particularly concern a method for treating a tumor wherein the method comprises administering at least one dose of a commercially available HPV vaccine to a patient having a tumor. Advantageously, the subject method has been found to be effective for treating a tumor in glandular tissue, such as breast, pituitary (e.g., invasive pituitary adenoma), prostate, or pancreas. This embodiment can include at administering at least one dose of the vaccine directly into the tumor, itself.

The subject invention can comprise administering at least one dose of the vaccine systemically, e.g., by intramuscular (IM) injection, alone, or in combination with (concomitantly or shortly before or after) the direct administration of the vaccine to the tumor.

Alternatively, in certain instances, e.g., when the tumor presents on or near the surface of the body, this method can further comprise topical administration of at least one dose of the HPV vaccine, alone, or in combination with direct injection into the tumor or in combination with systemic injection, or in combination with both direct and systemic injection.

Compositions comprising the vaccine are also included as part of the invention. For example, the HPV vaccine can be used or formulated with one or more additional active pharmaceutical ingredients for administration to the patient. Additional active pharmaceutical ingredients can be one or more immunomodulatory agent for modulating the effect of the vaccine, or one or more local anesthetic agent, e.g., lidocaine (with or without epinephrine), for reducing patient discomfort during the injection. A preferred embodiment can include the use of a first active agent which is an HPV vaccine and a second active agent which is an immunotherapy cancer drug, e.g., an Immune Checkpoint Inhibitors such as PD-1, PD-L1, or CTLA-4 inhibitors, or CAR T-cells. More preferably, the first and second active agents can be formulated together in a fixed-dose combination composition, namely, a composition comprising a therapeutically effective amount of an HPV vaccine such as GARDASIL, GARDASIL-9, CERVARIX, or the like, and a therapeutically effective amount of an Immune Checkpoint Inhibitor or CAR T-cells. Most preferably, the first and second active agents are formulated in an injectable dosage form.

One example of a composition of the invention comprises a 1:1 (v/v) ratio mixture of 0.5 ml of a commercially available HPV vaccine and 0.5 ml of a commercially available lidocaine solution (e.g., 0.5% (w/v), 1% (w/v), or 2% (w/v)). The composition can be thoroughly mixed and injected into a patient for treatment. Ratios ranging from 1:10 (v/v) vaccine:anesthetic solution to 10:1 (v/v) vaccine:anesthetic solution can be used, as would be understood in the art.

The HPV vaccine can also be formulated with one or more excipients or diluents for administration to the patient. Excipients and diluents can include one or more conventional pharmaceutically acceptable ingredients useful for formulating topical preparations, including but not limited to a bases for preparing a cream, emollient, gel, lotion, salve, or the like, and can optionally include penetration enhancers, preservatives, release-controlling agents, solubilizers, stabilizers, thickeners or thinners, or the like.

Solutions for injection can also include one or more buffer, emollient, diluent, pH adjuster, preservative, solubilizer, stabilizer, or the like.

These compositions can be prepared as a manufactured product which can be shipped, stored, and used as needed, including a later time, or can be compounded at the point of care or remotely for immediate single-use treatment.

A composition of the invention can include one or more additional active pharmaceutical ingredient without an excipient or diluent, or can include one or more active pharmaceutical ingredient and one or more excipient or diluent.

A composition of the invention can include one or more excipient or diluent without an additional active pharmaceutical ingredient, or can include one or more excipient or diluent and one or more active pharmaceutical ingredient.

To the knowledge of the inventor, administration of HPV vaccines comprising only HPV antigens (being free of host-cell peptides), to a previously unimmunized patient, or an adult patient aged 27 or greater, to eliminate or reduce the incidence of recurrence of skin cancer, benign or malignant tumor or other skin lesion that is not an HPV-associated lesion, has not been previously described. Nor has the direct or local administration of a vaccine by topical application or by direct injection into the lesion or tumor been previously described to eliminate the lesion and reduce the incidence of its recurrence.

DETAILED DESCRIPTION

The present invention is directed to a method of treating cancer, benign tumor, skin cancer, such as squamous cell carcinoma (SCC), or a skin lesion associated with or unassociated with human papilloma virus (HPV) infection, and includes treating a tumor originating in glandular tissue, such as breast, pituitary, prostate, or pancreatic tissue. One embodiment of a method in accordance with the subject invention comprises the administration of a commercially available HPV vaccine, such as an HPV quadrivalent (types 6, 11, 16, and 18) recombinant vaccine, to a patient having a cancer or tumor.

In one preferred embodiment, the subject method comprises administering at least one dose of the HPV vaccine to a patent that has not been previously immunized with an HPV vaccine, or to an adult patient aged 27 or older. For purposes of the subject invention, a patient previously not immunized with an HPV vaccine is termed an "unimmunized patient" regardless of other immunizations the patient may have received against other conditions or diseases.

The dosing regimen can be a single administration by direct injection, systemic injection, or topical application, or a combination of any of these administration routes. Alternatively, the subject method can comprise multiple (more than one) administration, or multiple (concomitant) administrations by direct injection, systemic injection, or topical application of the vaccine.

The subject method can also comprise administering in accordance with the conventionally accepted dosing series for a vaccine. For example, HPV vaccines are typically administered using a dosing regimen comprising a first dose, a second dose about two months following the first dose, and a third dose about six months following the first dose. These second, third, or subsequent administrations can be systemic injection, e.g., conventional intramuscular injection, or can be direct administration to the lesion by intralesional injection or by topical administration.

The method embodiments of the present invention have surprisingly been found to have beneficial results in treating, or minimizing the occurrence, recurrence, and/or progression of, cancer lesions or benign tumors that are not associated with HPV infection, such as basal-cell carcinoma (BBC) or melanoma.

While not being limited to any particular theory, it is proposed that the subject method can increase, i.e. boost a patient's immune response that may manifest clinically as increased surveillance in skin cells to decrease the likelihood of development and progression of abnormal skin cells that produce the skin cancer, particularly, but not exclusively, SCC.

Alternatively, the method of the invention can interfere with inherent functional activities of viral and virus-like proteins by other mechanisms. This interference would include the complete or partial functional inactivation of viral and virus-like materials altered or activated by exogenous and/or environmental agents such as ultraviolet light.

As used herein, the terms "HPV" and "human papillomavirus" refer to a non-enveloped, double-stranded DNA viruses of the papillomavirus family. Their genomes are circular and approximately 8 kilobase pairs in size. Most HPVs encode eight major proteins, six located in the "early" region (E1-E2) and two in the "late" region (L1 (the major capsid protein) and L2 (the minor capsid protein)). Over 120 HPV types have been identified, and they are designated by numbers (e.g., HPV-16, HPV-18, etc.).

In one embodiment, an HPV vaccine of the subject invention comprises one or more proteins (e.g., a recombinant L1 protein) from one, two, three, four, five, six, seven, eight, nine, ten or more different HPV types. Methods of expressing HPV L1 proteins and methods of making HPV vaccines are known in the art and described in, e.g., U.S. Pat. Nos. 5,820,870 and 6,251,678, which are incorporated herein by reference in their entireties for all purposes.

In one embodiment, the HPV vaccine employed in the subject method contains purified inactive viral or virus-like proteins, such as the commercially available GARDASIL®, which is an HPV quadrivalent (types 6, 11, 16, and 18) recombinant vaccine or GARDASIL® 9, an HPV multivalent (types 16, 18, 31, 33, 45, 52, and 58) recombinant vaccine. In another embodiment, the HPV vaccine is the commercially available CERVARIX®, which is an HPV bivalent (types 16 and 18) recombinant vaccine. A vaccine useful in accordance with this embodiment of the subject method is preferably free of host-cell and/or non-L1 HPV peptide, polypeptide, or protein, such as the early antigens, E6 or E7, which are fragments of host-cell peptides that present on the surface of an HPV-infected cell.

The vaccine can be administered for treating cancerous or benign tumors, including cancer lesions not associated with HPV infection, cancer (tumors or lesions) associated with HPV infection, benign tumors not associated with HPV infection, or non-cancerous HPV-related lesions in an unimmunized patient.

Alternatively, the vaccine can be administered to reduce the incidence of recurrence of cancer, a benign tumor, or an HPV-related lesion in an unimmunized patient. In another embodiment, the vaccine can be administered to treat cancer, benign tumor, or an HPV-related lesion, or reduce the incidence of recurrence thereof, in an adult patient aged 27 or greater.

More particularly, one preferred embodiment of the invention comprises a method for the treatment of cancer, benign tumor, or HPV-related lesion, in a patient that is unimmunized, or an adult patient aged 27 or older, comprising the steps of:
  i. administering to the patient a first dose of an HPV recombinant vaccine free of host-cell peptides, polypeptides, or proteins;
  ii. administering to the patient a second dose of the HPV recombinant vaccine free of host-cell peptides, polypeptides, or proteins between about one month and about three months after the first dose; and
  iii. optionally, administering to the patient a third dose of the HPV vaccine free of host-cell peptides, polypeptides, or proteins between about five months to about seven months after administering the first dose.

The second or third, or subsequent, administration of the vaccine dose can be systemic, e.g., intramuscular injection, or can be by direct administration to the lesion. The direct administration of the vaccine composition to the lesion can be by intralesional injection, or can be applied topically to the lesion. In a further embodiment, second, third or subsequent administrations are both systemic and by direct application of vaccine to the lesion. Such direct administration to the lesion can be intralesional injection or by topical application of a vaccine composition formulated for topical administration.

It would be understood by medical practitioners that the reference to the timing of subsequent administrations of the vaccine is approximate and can vary by days or even weeks. This variation can result from patient compliance or non-compliance to the scheduled dosing, clinical observation by the treating physician who may decide to advance (for more aggressive treatment) or delay a subsequent administration for medical reasons. Generally, however, an effective result can be achieved by following a dosing schedule where the second dose is administered about two months following the first dose, and a third dose at about six months after the first dose. Additional (fourth, or fifth) doses can be administered if the physician deems that subsequent administrations can provide benefit to the patient.

A typical total dose for each administration according to the method of the subject invention is about 0.5 ml of the vaccine, and is preferably 0.5 ml of a commercially available HPV vaccine.

The terms "cancer," "cancerous," or "malignant" refer to or describe the physiological condition in mammals that is typically characterized by unregulated cell growth. Examples of cancer include but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochondroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre tumor cervical dysplasia), ovaries (ovarian carcinoma [serous cystadenocarcinoma, mucinous cystadenocarcinoma, unclassified carcinoma], granulosa thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In another embodiment, the cancer is carcinoma, lymphoma, leukemia, blastoma, and sarcoma. More particular examples of such cancers include squamous cell carcinoma, myeloma, small-cell lung cancer, non-small cell lung cancer, glioma, Hodgkin's lymphoma, non-Hodgkin's lymphoma, acute myeloid leukemia (AML), multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, and head and neck cancer. In certain exemplary embodiments, a cancer is an HPV-associated cancer.

A particular example of cancer includes skin cancer, e.g., basal cell carcinoma and/or squamous cell carcinoma, among other known skin cancers. Another example of cancer includes breast cancer. Yet another example of cancer includes prostate cancer. Yet another example includes penile cancer. Yet another example of cancer includes ovarian, cervical, vaginal and/or vulvar cancer. Yet another example of cancer includes bladder cancer. Yet another example of cancer includes colorectal and/or anal cancer. Yet another example of cancer includes oropharyngeal cancer (e.g., cancer of the throat, soft palate, base of tongue, adenoids and/or tonsils). Yet another example of cancer includes renal cancer. Yet another example of cancer includes liver cancer.

In certain exemplary embodiments, a cancer is associated with decreased expression of Bcl-2-associated X protein (BAX) and/or Bcl-2 homologous antagonist/killer (BAK1). In other exemplary embodiments, a cancer is associated with one or more aberrant mitochondrial activities. In certain exemplary embodiments, an HPV vaccine of the invention increases BAX and/or BAK1 expression in a tumor cell and/or promotes apoptosis of the tumor cell. In other aspects, the combination of vitamin D and an HPV vaccine of the invention increases BAX and/or BAK1 expression in a tumor cell and/or promotes apoptosis of a tumor cell. In another embodiment, an HPV vaccine of the invention modulates one or more mitochondrial activities in a tumor cell.

The above embodiments of a method of treatment according to the subject invention can be efficacious for treating skin cancer in the patient, and particularly squamous cell carcinoma, wherein a skin cancer lesion is reduced in size or eliminated following the three administrations of the vaccine.

The treatment method in accordance with the subject invention can also reduce the incidence of recurrence of benign tumors or cancer tumors or lesions, including skin cancer, in the patient.

In particular the treatment method according to the subject invention comprises eliminating, or reducing the size or incidence of recurrence of a cancerous tumor of the breast, eliminating, or reducing the size or incidence of recurrence in a cancerous tumor of the prostate, eliminating, or reducing the size or incidence of recurrence of a cancerous tumor of the pancreas, or eliminating, or reducing the size or incidence of recurrence of a cancerous tumor of the pituitary gland, e.g., invasive pituitary adenoma.

Other particular types of cancers or tumors that can benefit from treatment using an HPV vaccine in accordance with the method of the subject invention include, and are not limited to, cervical cancer, anal cancer, oropharyngeal cancers (throat, soft palate, base of tongue, or tonsils), vaginal cancer, vulvar cancer, penile cancer, colorectal cancer, bladder cancer, lung cancer, renal cancer, liver cancer, ovarian cancer, pancreatic mucinous cystic neoplasms, gastric or stomach cancer.

The method according to the subject invention can also be effective to reduce the size or eliminate an HPV-associated, but non-cancerous, lesion, such as warts, including genital warts, e.g., verruca vulgaris or condyloma accuminata.

It is a further unexpected result of the present invention to provide a method of reducing the incidence of recurrence of skin cancer, and particularly squamous cell carcinoma following administration of one or more injections of HPV quadrivalent (types 6, 11, 16, and 18) recombinant vaccine, wherein the vaccine is substantially free of host-cell peptides, polypeptides, or proteins which, as a result of HPV infection of the cell, present on the surface of the infected cell. Further unexpected results of the subject method of treatment comprise reducing the size of, eliminating, or reducing the incidence of recurrence of skin lesions that are not associated with HPV infection, such as basal cell carcinoma or melanoma.

The invention pertains to uses of the above-described agents for the therapeutic treatment of cancer. Accordingly, an HPV vaccine composition of the present invention is incorporated into pharmaceutical compositions suitable for administration. Such compositions typically comprise an HPV viral or viral-like protein and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous (IV), intradermal, subcutaneous (SC or SQ), intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, or by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier to be swallowed or ingested as a solution or suspension, or for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the HPV viral or viral-like proteins are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack, or dispenser together with optional instructions for administration.

The route of delivery can be dependent on the disorder of the patient. In certain exemplary embodiments, a subject diagnosed with skin cancer can be administered an HPV vaccine composition of the invention by topical administration. In addition to an HPV vaccine composition of the invention, a patient can be administered a second therapy, e.g., a palliative therapy and/or disease-specific therapy. The secondary therapy can be, for example, symptomatic (e.g., for alleviating symptoms), protective (e.g., for slowing or halting disease progression), or restorative (e.g., for reversing the disease process). For the treatment of cancer, for example, symptomatic therapies can further include another chemotherapeutic agent used as a combination therapy as described further herein.

In general, an HPV vaccine composition of the invention can be administered by any suitable method. As used herein, topical delivery can refer to the direct application of an HPV vaccine composition to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver an HPV vaccine composition to the epidermis or dermis of a subject, or to specific strata thereof, or to an underlying tissue.

Formulations for parenteral administration may include sterile aqueous solutions which may also contain buffers, diluents, and other suitable additives. Intraventricular injection may be facilitated by an intraventricular catheter, for example, attached to a reservoir. For intravenous use, the total concentration of solutes should be controlled to render the preparation isotonic.

An HPV vaccine composition of the invention can be administered to a subject by pulmonary delivery. Pulmonary delivery compositions can be delivered by inhalation of a dispersion so that the composition within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self-contained. Dry powder dispersion devices, for example, deliver drugs that may be readily formulated as dry powders. An HPV vaccine composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The types of pharmaceutical excipients that are useful as carriers include stabilizers such as Human Serum Albumin (HSA), bulking agents such as carbohydrates, amino acids, and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids, or combinations thereof. Suitable carbohydrates include monosaccharides such as galactose, D-mannose, sorbose, and the like; disaccharides, such as lactose, trehalose, and the like; cyclodextrins, such as 2-hydroxypropyl-β-cyclodextrin; and polysaccharides, such as raffinose, maltodextrins, dextrans, and the like; alditols, such as mannitol, xylitol, and the like. A preferred group of carbohydrates includes lactose, trehalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

One or more HPV viral or viral-like proteins of the invention (i.e., an HPV vaccine) can be administered by oral or nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized, and removed easily.

Another embodiment in accordance with the subject invention comprises administering an HPV vaccine administered to a patient by direct or local administration, e.g., injection, into a skin lesion or surrounding area of the lesion. This direct administration method can be useful in patients suffering from cancer, particularly skin cancer. This embodiment of the method can also be useful for treating non-cancerous (benign) tumors, or non-cancerous lesions associated with HPV, such as warts, e.g., verruca vulgaris or condyloma accuminata.

In an embodiment comprising direct injection into or surrounding a lesion, the dosing regimen can comprise a single administration or more than one administration. For example, a three-administration dosing series, as above, can be followed. Alternatively, a physician can administer a subsequent dose as needed (prn) following an initial dose directly into or surrounding the lesion. Divided dosing of the vaccine for any particular single time point is considered to be a single administration.

This direct-administration embodiment of the invention can have beneficial results in treating, or minimizing the occurrence, recurrence, and/or progression of, cancer lesions or tumors such as basal-cell carcinoma (BBC) or melanoma, or non-cancerous (benign) tumors that are not associated with HPV infection.

In one embodiment of the subject invention, the method is carried out without the administration of an additional or other immunostimulant or adjuvant either with, during, or following the treatment method of the invention.

Alternatively, the subject method can comprise administering an additional or other immunomodulatory agent, e.g., and immunostimulant or adjuvant, with, during or following the administration of the vaccine. Non-limiting examples of immunomodulatory agents useful as part of the subject method include:
1) Vitamin D and its analogues;
2) Sirolimus;
3) Interferon and its analogues;
4) Vitamin A and its analogues, e.g., Soriatane (a retinoid)
5) Imiquimod;
6) Ingenol mebutate; and
7) T4 endonuclease
8) Antimetabolites, e.g. 5 Fluorouracil, Methotrexate
9) Cyclooxygenase inhibitors, e.g. Diclofenac These agents can be given in combination locally or systemically with, or contemporaneous with, the HPV vaccine as described herein, to enhance the effect of the treatment. For example, in a previously HPV immunized patient having a tumor (skin, lung, or the like), a combination of interferon and HPV antigen vaccine could be given locally. Interferon may or may not also be given at the same time systemically. This administration can enhance local destruction of the tumor or other lesion without the systemic side effects associated with interferon.

In another aspect of the invention, the invention provides a method for treating cancer in an individual comprising administering to the individual a combination therapy which comprises an HPV vaccine and one or more additional chemotherapeutic agents other than the HPV vaccine. The specific dosage and dosage schedule of the additional therapeutic agent can further vary, and the optimal dose, dosing schedule and route of administration will be determined based upon the specific therapeutic agent that is being used.

Examples of chemotherapeutic agents include alkylating agents such as thiotepa and cyclosphosphamide; alkyl sulfonates such as busulfan, improsulfan and piposulfan; aziri dines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; cally statin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancrati statin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gammall and calicheamicin phill, see, e.g., Agnew, Chem. Intl. Ed. Engl., 33: 183-186 (1994); dynemicin, including dynemicin A; bisphosphonates, such as clodronate; an esperamicin; as well as neocarzinostatin chromophore and related chromoprotein enediyne antibiotic chrommophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylormthine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; and pharmaceutically acceptable salts, acids or derivatives of any of the above.

In one preferred embodiment, a method of treatment according to the invention comprises administering a first active agent being an HPV vaccine as described herein, and a second active agent which is an Immune Checkpoint Inhibitor or CAR T-cells. An Immune Checkpoint Inhibitor can include a Programed Death 1 (PD-1) inhibitor; or a Programed Death 1 Ligand (PD-1L) inhibitor. Examples of PD-1 and PD-1L inhibitors are:

Cemiplimab
Atezolizumab
Avelumab
Bavencio
Durvalumab
Imfinzi
Keytruda
Nivolumab
Opdivo
Pembrolizumab, and
Tecentriq An example of a Cytotoxic T-lymphocyte-Associated Protein 4 (CTLA-4) inhibitor is Ipilumumab.

CAR T-cells is the abbreviation for Chimeric Antigen Receptor T cells and can include a bispecific antibody, such as Catumaxomab, or a monoclonal antibody, such as Campath, Brutuximab, Vismodigib, or the BRAF inhibitors, Vemurafenib, Dabrfenib, or ecorafenib. In view of the limitations of these immune-based therapies, alone, or in combination with one another, an HPV vaccine, being inhibitory on multiple levels, can advantageously boost eh efficacy of the immune-based therapy. Vaccination to HPV infection results in resistance to a naturally occurring, commonly encountered, infectious agent and can unexpectedly provide an immune response more complex than inhibition of a select few pathways as produced by immune-based therapies, used alone. The response to vaccine seen in elderly patients indicates an immune based effect in subjects with failing immune surveillance function. Intralesional injection of HPV vaccine also indicates a direct local effect on treated tumors.

Each therapeutic agent in a combination therapy of the invention may be administered either alone or in a medicament (also referred to herein as a pharmaceutical composition or a fixed-dose combination product) which comprises the therapeutic agent and one or more pharmaceutically acceptable carriers, excipients and diluents, according to standard pharmaceutical practice.

Each therapeutic agent in a combination therapy of the invention may be administered simultaneously (i.e., in the same medicament), concurrently (i.e., in separate medicaments administered one right after the other in any order) or sequentially in any order. Sequential administration is particularly useful when the therapeutic agents in the combination therapy are in different dosage forms (one agent is a tablet or capsule and another agent is a sterile liquid) and/or are administered on different dosing schedules, e.g., a chemotherapeutic that is administered at least daily and an HPV vaccine that is administered less frequently, such as once weekly, once every two weeks, or once every three weeks.

In some embodiments, the HPV vaccine is administered before administration of the chemotherapeutic agent, while in other embodiments, the HPV vaccine is administered after administration of the chemotherapeutic agent. In another embodiment, the HPV vaccine is administered concurrently with the chemotherapeutic agent.

In some embodiments, at least one of the therapeutic agents in the combination therapy is administered using the same dosage regimen (dose, frequency, and duration of treatment) that is typically employed when the agent is used as monotherapy for treating the same cancer. In other embodiments, the patient receives a lower total amount of at least one of the therapeutic agents in the combination therapy than when the agent is used as monotherapy, e.g., smaller doses, less frequent doses, and/or shorter treatment duration.

Each therapeutic agent in a combination therapy of the invention can be administered orally or parenterally, including the intravenous, intramuscular, intraperitoneal, subcutaneous, rectal, topical, and transdermal routes of administration.

A combination therapy of the invention may be used prior to or following surgery to remove a tumor and may be used prior to, during or after radiation therapy.

In some embodiments, a combination therapy of the invention is administered to a patient who has not been previously treated with a biotherapeutic or chemotherapeutic agent, i.e., is treatment-naive. In other embodiments, the combination therapy is administered to a patient who failed to achieve a sustained response after prior therapy with a biotherapeutic or chemotherapeutic agent, i.e., is treatment-experienced.

A combination therapy of the invention is typically used to treat a tumor that is large enough to be found by palpation, visual observation or by imaging techniques well known in the art, such as MRI, ultrasound, or CAT scan.

Any commercially available HPV vaccine can be employed for administration directly to a cancer or HPV-related lesion. For example, this embodiment of the subject method can comprise directly administering into or surrounding a lesion, a vaccine comprising purified inactive viral or virus-like proteins, such as the commercially available GARDASIL®, which is an HPV quadrivalent (types 6, 11, 16, and 18) recombinant vaccine or GARDASIL® 9, an HPV multivalent (types 16, 18, 31, 33, 45, 52, and 58)

recombinant vaccine or CERVARIX®, an HPV bivalent (types 16 and 18) recombinant vaccine.

A vaccine useful in accordance with this embodiment of the subject method can include host-cell peptides, polypeptides, or proteins, such as the early antigens, E6 or E7 or exclude or be free of host-cell peptides, polypeptides, or proteins, such as the early antigens, E6 or E7. The vaccine can be administered for treating cancer, a benign tumor, or HPV-related lesion in a patient of any age, whether an unimmunized patient or a patient previously immunized with an HPV vaccine.

The vaccine can be directly or locally administered into or surrounding a lesion or tumor to reduce the incidence of recurrence of cancer, benign tumor, or an HPV-related lesion in a patient.

In another embodiment, the vaccine can be administered to treat cancer, benign tumor, or an HPV-related lesion, or reduce the incidence of recurrence thereof, in a patient up to 26 years old (e.g., an infant, a child, an adolescent or a young adult) or, alternatively, an adult patient aged 27 or greater.

More particularly, one preferred embodiment of the invention comprises a method for the treatment of cancerous or non-cancerous tumor or lesion in a patient comprising the step of administering to the patient a dose of an HPV recombinant vaccine directly to the lesion, tumor, or non-cancerous HPV-related lesion.

Alternatively, the method can comprise the following optional steps:
i. administering directly to a cancer lesion, benign tumor, or non-cancerous HPV-related lesion of a patient a second dose of the HPV vaccine between about one month and about three months after the first dose;
ii. administering directly to a cancer lesion, benign tumor, or non-cancerous HPV-related lesion of a patient a subsequent dose of the HPV vaccine between about five months to about seven months after administering the first dose; or
iii. administering directly to a cancer lesion, benign tumor, or non-cancerous HPV-related lesion of a patient a second dose of the HPV vaccine between about one month and about three months after the first dose, and administering directly to a cancer lesion, benign tumor, or non-cancerous HPV-related lesion of a patient a subsequent dose of the HPV vaccine between about five months to about seven months after administering the first dose.

It would be understood by medical practitioners that the reference to the timing of subsequent administrations of the vaccine is approximate and can vary by days or even weeks. This variation can result from patient compliance or non-compliance to the scheduled dosing, clinical observation by the treating physician who may decide to advance (for more aggressive treatment) or delay a subsequent administration for medical reasons. Generally, however, an effective result can be achieved by following a dosing schedule where the second dose is administered about two months following the first dose, and a third dose at about six months after the first dose. Additional (fourth, or fifth) doses can be administered if the physician deems that subsequent administrations can provide benefit to the patient.

Selecting a dosage regimen (also referred to herein as an administration regimen) depends on several factors, including the serum or tissue turnover rate of the entity, the level of symptoms, the immunogenicity of the entity, and the accessibility of the target cells, tissue or organ in the individual being treated. Preferably, a dosage regimen maximizes the amount of therapeutic agent delivered to the patient consistent with an acceptable level of side effects. Accordingly, the dose amount and dosing frequency depends in part on the particular therapeutic agent, the severity of the cancer being treated, and patient characteristics. Guidance in selecting appropriate doses of antibodies, cytokines, and small molecules are available. See, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, NY; Bach (ed.) (1993) Monoclonal Antibodies and Peptide Therapy in Autoimmune Diseases, Marcel Dekker, New York, NY; Baert et al. (2003) New Engl. J. Med. 348:601-608; Milgrom et al. (1999) New Engl. J. Med. 341: 1966-1973; Slamon et al. (2001) New Engl. J. Med. 344: 783-792; Beniaminovitz et al. (2000) New Engl. J. Med. 342:613-619; Ghosh et al. (2003) New Engl. J. Med. 348: 24-32; Lipsky et al. (2000) New Engl. J. Med. 343: 1594-1602; Physicians' Desk Reference 2003 (Physicians' Desk Reference, 57th Ed); Medical Economics Company; ISBN: 1563634457; 57th edition (November 2002). Determination of the appropriate dosage regimen may be made by the clinician, e.g., using parameters or factors known or suspected in the art to affect treatment or predicted to affect treatment, and will depend, for example, the patient's clinical history (e.g., previous therapy), the type and stage of the cancer to be treated and biomarkers of response to one or more of the therapeutic agents in the combination therapy.

HPV viral or viral-like proteins of the invention may be administered by continuous infusion, or by doses at intervals of, e.g., daily, every other day, three times per week, or one time each week, two weeks, three weeks, monthly, bimonthly, etc. A total weekly dose is generally at least 0.05 µg/kg, 0.2 µg/kg, 0.5 µg/kg, 1 µg/kg, 10 µg/kg, 100 µg/kg, 0.2 mg/kg, 1.0 mg/kg, 2.0 mg/kg, 10 mg/kg, 25 mg/kg, 50 mg/kg body weight or more. See, e.g., Yang et al. (2003) New Engl. J. Med. 349:427-434; Herold et al. (2002) New Engl. J. Med. 346: 1692-1698; Liu et al. (1999) J. Neurol. Neurosurg. Psych. 67:451-456; Portielji et al. (20003) Cancer Immunol. Immunother. 52: 133-144.

In some embodiments, the dosing regimen will comprise administering the HPV vaccine at a dose of 1, 2, 3, 5 or 10 mg/kg at intervals of about 14 days (±2 days) or about 21 days (±2 days) or about 30 days (±2 days) or about one week (±2 days), two weeks (±2 days), three weeks (±2 days) or four weeks (±2 days) throughout the course of treatment.

In other embodiments, the dosing regimen will comprise administering the HPV vaccine at a dose of from about 0.005 mg/kg to about 10 mg/kg, with intra-patient dose escalation. In other escalating dose embodiments, the interval between doses will be progressively shortened, e.g., about 30 days (±2 days) between the first and second dose, about 14 days (±2 days) between the second and third doses. In certain embodiments, the dosing interval will be about 14 days (±2 days), for doses subsequent to the second dose. A typical total dose for each direct or local administration according to the method of the subject invention is about 0.5 ml of the vaccine, e.g., of a commercially available vaccine. Each 0.5 ml dose can be administered, e.g., by intralesional injection, as a bolus of the entire 0.5 ml or can be administered as a divided dose as a plurality of 0.1-0.2 ml partial administrations into the lesion, an area surrounding the lesion, or both.

According to certain embodiments, multiple doses of an HPV vaccine may be administered to a subject over a defined time course. The methods include, for example, sequentially administering to a subject multiple doses of an HPV vaccine. As used herein, "sequentially administering" means that each dose of an HPV vaccine is administered to the subject at a different point in time, e.g., on different days separated by a predetermined interval (e.g., hours, days, weeks, or months). The present invention includes methods which comprise sequentially administering to the patient a single initial dose of an HPV vaccine, followed by one or more secondary doses of an HPV vaccine, and optionally followed by one or more tertiary doses of an HPV vaccine.

The terms "initial dose," "secondary doses," and "tertiary doses," refer to the temporal sequence of administration of an HPV vaccine. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of an HPV vaccine (e.g., of the one or more HPV viral or viral-like proteins), but will generally differ from one another in terms of frequency of administration. In certain embodiments, however, the amount of an HPV vaccine (e.g., of the one or more HPV viral or viral-like proteins) contained in the initial, secondary and/or tertiary doses will vary from one another (e.g., adjusted up or down as appropriate) during the course of treatment.

In one exemplary embodiment, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. In another exemplary embodiment, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) months after the immediately preceding dose. The phrase "the immediately preceding dose," as used herein, means, in a sequence of multiple administrations, the dose of an HPV vaccine which is administered to a patient prior to the administration of the very next dose in the sequence with no intervening doses.

These methods may include administering to a patient any number of secondary and/or tertiary doses of an HPV vaccine. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 3 months after the immediately preceding dose. Similarly, in embodiments involving multiple tertiary doses, each tertiary dose may be administered at the same frequency as the other tertiary doses. For example, each tertiary dose may be administered to the patient 1 to 3 months after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

In certain embodiments, the initial dose (e.g., a "loading dose") is higher than either or both of the secondary and tertiary doses. For example, the initial dose can be a loading dose, which is 1.5×, 2×, 2.5×, 3× or more, greater than the secondary dose.

The above direct or local administration method of treatment can be efficacious for treating skin cancer in the patient, and particularly squamous cell carcinoma, wherein a skin cancer lesion is reduced in size or eliminated following the three administrations of the vaccine.

The direct or local administration treatment method according to the subject invention can also reduce the incidence of recurrence of cancer, including skin cancer, in the patient.

The direct or local administration method can also be effective to reduce the size or eliminate a benign tumor, whether or not associated with HPV infection, or an HPV-associated, but non-cancerous, lesion, such as warts, including genital warts, e.g., verruca vulgaris or condyloma accuminata.

The direct or local administration method can also be effective to reduce the incidence of recurrence of a benign tumor, whether or not associated with HPV infection, or an HPV-associated, but non-cancerous, lesion, such as warts, including genital warts, e.g., verruca vulgaris or condyloma accuminata.

It is a further unexpected result of the present invention to provide a method of eliminating or reducing the size or incidence of recurrence of skin cancer, and particularly squamous cell carcinoma following direct or local administration of one or more injections of HPV bivalent (types 16 and 18) recombinant vaccine, HPV quadrivalent (types 6, 11, 16, and 18) recombinant vaccine or an HPV multivalent (types 16, 18, 31, 33, 45, 52, and 58) recombinant vaccine.

Further unexpected results of the subject direct or local administration method of treatment comprise reducing the size of, eliminating, or reducing the incidence of recurrence of skin lesions that are not associated with HPV infection, such as basal cell carcinoma or melanoma.

In one embodiment of the subject invention, the direct or local administration method is carried out without the administration of an additional or other immunostimulant or adjuvant.

In certain embodiments, the subject method can comprise administering an additional or other immunomodulatory agent, e.g., and immunostimulant or adjuvant, with, during or following the administration of the vaccine. Non-limiting examples of immunomodulatory agents useful as part of the subject method include:

1) Vitamin D and its analogues;
    2) Sirolimus;
    3) Interferon and its analogues;
    4) Vitamin A and its analogues, e.g., Soriatane (a retinoid)
    5) Imiquimod;
    6) Ingenol mebutate; and
    7) T4 endonuclease
    8) Antimetabolites, e.g. 5 Fluorouracil, Methotrexate
    9) cyclooxygenase inhibitors, e.g. Diclofenac These agents can be given in combination locally or systemically with, or contemporaneous with, the HPV vaccine as described herein, to enhance the effect of the treatment. For example, in a previously HPV immunized patient having a tumor (skin, lung, or the like), a combination of interferon and HPV antigen vaccine could be given locally. Interferon may or may not also be given at the same time systemically. This administration can enhance local destruction of the tumor or other lesion without the systemic side effects associated with interferon.

Topical application can be beneficial for several reasons, including the elimination of infection risk caused by injection, but can also be advantageous by wide-spread application over large areas in order to treat precancerous (actinic keratoses) as well as malignant tumors. In addition, the topical administration can provide cosmetic enhancement of the skin, by decreasing that appearance of pigment irregularities, poikiloderma, and scaling.

It is therefore an object of the subject invention to provide a cost-effective, safe, efficacious, and convenient treatment for reducing or ameliorating the growth or size of a cancer tumor or lesion, including a skin cancer lesion such as SCC, BCC or melanoma tumor or lesion. It is another object of the subject invention to provide a cost-effective, efficacious and convenient treatment for curing skin cancer lesions, and yet another object of the invention to provide a cost-effective, efficacious and convenient method to reduce the incidence of recurrence of cancer, including skin cancer lesions.

The subject method of treating or reducing the incidence of recurrence of skin cancer comprises administering an HPV vaccine in one or more doses to a patient. In one embodiment, the method includes administration of a first dose of HPV quadrivalent (types 6, 11, 16, and 18) recombinant vaccine to a patient, a second dose of HPV quadrivalent (types 6, 11, 16, and 18) recombinant vaccine approximately two months thereafter, and a third dose of HPV quadrivalent (types 6, 11, 16, and 18) recombinant vaccine approximately four months after the second dose. In a preferred embodiment, each dose is 0.5 ml.

The subject method can be advantageous in that it can be performed using a commercially available HPV bivalent (types 16 and 18) recombinant vaccine, HPV quadrivalent (types 6, 11, 16, and 18) vaccine or HPV multivalent (types 16, 18, 31, 33, 45, 52, and 58) recombinant vaccine as a therapeutic agent rather than or in addition to its use as a preventive vaccine.

A preventive vaccine is understood to be a vaccine composition administered prior to exposure to or infection with an agent such as human papilloma virus (HPV). Preventive vaccines for protection against or prevention of HPV infection and associated cancers are commercially available are therefore known to be safe. GARDASIL® is an HPV quadrivalent (types 6, 11, 16, and 18) recombinant vaccine and GARDASIL® 9, is an HPV multivalent (types 16, 18, 31, 33, 45, 52, and 58) recombinant vaccine currently marketed as a preventive vaccine in the United States by Merck & Co., Inc. Whitehouse Station, NJ 08889 USA. CERVARIX® is an HPV bivalent (types 16 and 18) recombinant vaccine available from GlaxoSmithKline (Brentford, England).

By use of a commercially available vaccine, the vaccine can be readily accessed by a physician or healthcare practitioner. Moreover, the use of an HPV bivalent (types 16 and 18) recombinant vaccine, an HPV quadrivalent (types 6, 11, 16, and 18) recombinant vaccine or HPV multivalent (types 16, 18, 31, 33, 45, 52, and 58) recombinant vaccine in accordance with the subject method do not require secondary or additional immunostimulants or adjuvants. These commercially available HPV bivalent (types 16 and 18), HPV quadrivalent (types 6, 11, 16, and 18) or HPV multivalent (types 16, 18, 31, 33, 45, 52, and 58) recombinant vaccines are free, or substantially free, of host-cell and/or non-L1 viral peptides, polypeptides, or proteins, such as the antigens, E6 or E7.

Advantageously, the unexpected result of treating cancer, benign tumor, or HPV-related skin lesions, including skin cancers that are associated with HPV infection or skin cancers that are not associated with HPV infection, can be achieved using the subject method as described herein.

Another embodiment of the subject invention includes a composition for carrying out a method of treatment as described. Compositions comprising the vaccine and an added ingredient—one or more of an active pharmaceutical ingredient, excipient, or diluent, for example—are also included as part of the invention. In a composition of the invention, HPV vaccine can be formulated with one or more additional active pharmaceutical ingredients for administration to the patient. Additional active pharmaceutical ingredients can be one or more immunomodulatory agent for modulating the effect of the vaccine, or one or more local anesthetic agent, e.g., lidocaine (with or without epinephrine), for reducing patient discomfort during the injection.

One embodiment of a composition of the subject invention comprises commercially available HPV vaccine formulated with one or more immunomodulatory agent. The one or more immunomodulatory agent can be selected from the group consisting of:

1) Vitamin D and its analogues;
2) Sirolimus;
3) Interferon and its analogues;
4) Vitamin A and its analogues, e.g., Soriatane (a retinoid)
5) Imiquimod;
6) Ingenol mebutate; and
7) T4 endonuclease
8) Antimetabolites, e.g. 5 Fluorouracil, Methotrexate
9) cyclooxygenase inhibitors, e.g. Diclofenac A composition comprising HPV vaccine and at least one immunomodulatory agent can advantageously provide enhanced effect of the anti-cancer therapeutic activity of the HPV vaccine.

One embodiment of a composition of the subject invention comprises commercially available HPV vaccine formulated with one or more local anesthetic agent. The one or more local anesthetic agent can be selected from the group consisting of: the ester local anesthetics, namely procaine, benzocaine, chloroprocaine, cocaine, cyclomethycaine, dimethocaine/larocaine, piperocaine, propoxycaine, procaine, proparacaine, and tetracaine, or the amide local anesthetics, namely, lidocaine, articaine, bupivacaine, cinchocaine, etidocaine, levobupivacaine, lignocaine, mepivacaine, prilocaine, ropivacaine, and trimecaine.

One example of a composition of the invention comprises a 1:1 (v/v) ratio mixture of 0.5 ml of a commercially available HPV vaccine and 0.5 ml of a commercially available lidocaine solution (e.g., 0.5% (w/v), 1% (w/v), or 2% (w/v)). The composition can be thoroughly mixed and injected into a patient for treatment. Ratios ranging from 1:10 (v/v) vaccine:anesthetic solution to 10:1 (v/v) vaccine:anesthetic solution can be used, as would be understood in the art.

One embodiment of a composition of the subject invention comprises commercially available HPV vaccine formulated in a fixed-dose combination product with one or more anti-cancer agent selected from the group consisting of an Immune Checkpoint Inhibitors and CAR T-cells.

Immune Checkpoint Inhibitors of the invention include, but are not limited to, the PD-1/PD-L1 Inhibitors Cemiplimab, Atezolizumab, Avelumab, Bavencio, Durvalumab, Imfinzi, Keytruda, Nivolumab, Opdivo, Pembrolizumab, and Tecentriq, or can include the CRLA-4 inhibitor Ipilumumab. CAR T-cells that can be formulated in a fixed-dose combination product with HPV vaccine include bispecific antibodies, such as Catumaxomab; monoclonal antibodies, such as Campath, Brutuximab, or Vismodigib, or the BRAF inhibitors, Vemurafenib, Dabrfenib, or ecorafenib.

The HPV vaccine and second active agent such as Immune Checkpoint Inhibitors and CAR T-cells can also be formulated with one or more excipients or diluents for administration to the patient. Solutions for injection can also include one or more buffer, emollient, diluent, pH adjuster, preservative, solubilizer, stabilizer, or the like.

Excipients and diluents can include one or more conventional pharmaceutically acceptable ingredients useful for formulating topical preparations, including but not limited to, a base for preparing a cream, emollient, gel, lotion, salve, or the like, and can optionally include penetration enhancers, preservatives, release-controlling agents, solubilizers, stabilizers, thickeners or thinners, or the like.

A topical composition comprising a vaccine useful in accordance with the subject invention can be formulated as is conventionally known in the pharmaceutical arts, and can comprise one or more additional ingredients or excipients, such as an organic or inorganic solvent (aqueous or non-aqueous), stabilizing agent, penetration enhancer, buffer, gelling agent, polymeric agent, lubricant, glidant, cream, wax, suspending agent, surfactant, or the like. The formulation can further include a penetration enhancer, such as DMSO. The formulation can be provided as a topical solution, lotion or shake lotion, ointment, cream, gel, foam, transdermal patch, biofrequency chip, powder, solid, sponge, tape, paste, tincture, micelle or liposome, or the like.

These compositions can be prepared as a manufactured product which can be shipped, stored, and used as needed, including a later time, or can be compounded at the point of care or remotely for immediate single-use treatment.

A composition of the invention can include one or more additional active pharmaceutical ingredient without an excipient or diluent, or can include one or more active pharmaceutical ingredient and one or more excipient or diluent.

A composition of the invention can include one or more excipient or diluent without an additional active pharmaceutical ingredient, or can include one or more excipient or diluent and one or more active pharmaceutical ingredient

EXAMPLES

Example 1—Skin Cancer

The following charts provide the results from the subject method of treatment carried out in three patients experiencing relatively frequent recurrence rates of skin cancer, including squamous cell carcinoma (SCC) as well as basal-cell carcinoma.

The data presented below represents an average number of distinctive recurrences of skin cancer per month for a period of time prior to and after undergoing the method of treatment described herein.

A. Patient 1

Patient 1 was administered three 0.5 ml doses, including a first 0.5 ml dose, a second 0.5 ml dose two months later, and a third 0.5 ml dose four months after the second dose. In a follow-up exam three months after administration of the third dose of HPV quadrivalent (types 6, 11, 16, and 18) recombinant vaccine, Patient 1 had experienced zero recurrences of skin cancer, including both SCC and BCC types, during the three-month period. Prior to commencement of the treatment method, Patient 1 had more than 300 distinctive occurrences of skin cancer during his lifetime.

Patient 1

| | Time Period (Months) | SCC | BCC |
|---|---|---|---|
| Prior to Commencement of Treatment Method | 16 | 1.80 | 0.25 |
| After Commencement of Treatment Method | 16 | 0.37 | 0.00 |

B. Patient 2

Patient 2 was administered three 0.5 ml doses of HPV quadrivalent (types 6, 11, 16, and 18) recombinant vaccine, including a first 0.5 ml dose, a second 0.5 ml dose two months later, and a third 0.5 ml dose four months after the second dose.

Patient 2

| | Time Period (Months) | SCC | BCC |
|---|---|---|---|
| Prior to Commencement of Treatment Method | 13 | 2.07 | 0.53 |
| After Commencement of Treatment Method | 13 | 0.23 | 0.3 |

C. Patient 3

Patient 3 was administered three 0.5 ml doses of HPV quadrivalent (types 6, 11, 16, and 18) recombinant vaccine, including a first 0.5 ml dose, a second 0.5 ml dose two months later, and a third 0.5 ml dose eight months after the second dose.

Patient 3

| | Time Period (Months) | SCC | BCC |
|---|---|---|---|
| Prior to Commencement of Treatment Method | 22 | 0.18 | 0.13 |
| After Commencement of Treatment Method | 22 | 0.09 | 0.04 |

As a group, each of the patients who underwent the method of treatment using HPV quadrivalent (types 6, 11, 16, and 18) recombinant vaccine experienced a significant decrease in the number of skin cancer recurrences, as well as improvement in the texture and appearance of the skin with decreased scaling and an increase in general skin suppleness.

Generally, the method of treatment described herein serves to effectively increase, i.e. boost, the patient's immune surveillance in skin cells in order to decrease the likelihood of a development of abnormal skin cells that produce the skin cancer. The method of the present invention has been shown to treat and prevent recurrence of SCC, and to significantly reduce recurrence of BCC. It is also possible that the increase in immune surveillance, as a result of the treatment method, will concomitantly decrease the incidence of malignant melanoma.

In one embodiment, the method of treatment for eliminating or reducing the incidence of recurrence of skin cancer includes administering the HPV quadrivalent (types 6, 11, 16, and 18) recombinant vaccine in the form of an injection directly into the cancerous tissue or an area of tissue immediately surrounding the cancerous tissue.

Example 2—Breast Cancer

A previously HPV-vaccinated 32-year old woman with no history of breast cancer, no family history, and no risk factors, was diagnosed with metastatic breast cancer. Her main tumor was measured by ultrasound as being about 4.1 centimeters in diameter. These metastatic tumors can double in size in about 12 weeks.

With the patient's fully informed consent and knowledge, the tumor was directly injected with a standard initial dose (about 0.5 ml) of a commercially available HPV vaccine. A second dose 0.5 ml, diluted with saline and lidocaine to about 3 ml, was directly administered to the tumor about two weeks after the first injection. At that time, it was harder to find the tumor to inject, and was believed to have been reduced in size.

A follow up ultrasound recently showed that the tumor had been reduced in size to about 2.7 centimeters in diameter, corresponding to an approximate 35% reduction in diameter, and a 75% reduction in tumor volume (volume for a sphere is calculated as 4/3 pi×radius cubed).

With the expected doubling of size, the tumor should have increased by about 40%. to a tumor diameter of about 4.6 centimeters.

Example 3—Metastatic Basosquamous Carcinoma

A 99-year old female presented with metastatic basosquamous carcinoma on the leg. metastatic basosquamous carcinoma, severe enough that she was referred to dermatology for palliative treatment and no further options were available but amputation of the limb to prevent further spreading of the cancer.

A single injection of a conventional dose (about 0.5 ml) of a commercially available HPV vaccine was administered to the patient, intramuscularly (systemically). Additional standard doses of the HPV vaccine were injected into each of two or more sites of the larger lesions.

Within four weeks of the treatment with HPV vaccine, the lesions were substantially visually improved, and the cancer had no further spreading on the leg. The patient is currently in remission from further or increased size of the lesions.

Example 4—Penile Cancer

A 45 year old HIV-positive man with a two-year history of squamous cell carcinoma of the penis that was recalcitrant to treatment with a variety of topical and surgical methods was treated with three equal doses of GARDASIL®, intramuscularly, in accordance with the label instructions.

Within four days, the patient's pain started to lessen, from a pain scale rating of 9-10 on a 10-scale rating to zero over the course of several weeks.

Recent examinations with confocal microscopy show no evidence of malignancy. Confocal photography can be used to detect cancer on skin without the need for biopsy.

Example 5—Aggressive Squamous Cell Carcinoma

An aggressive rapidly growing recurrent squamous cell carcinoma on the lower extremity of an elderly man with history of renal cell carcinoma, and history of chemotherapy was treated with two intralesional injections of GARDASIL® mixed with lidocaine 1% with epinephrine.

The patient had previously been inoculated with GARDASIL® intramuscularly.

This tumor completely regressed and involuted soon after the first treatment, with no further evidence of malignancy.

Example 6—Prostate Cancer

Prostate cancer treatment would involve treating the patient with intramuscular HPV, and can also include direct injection into the prostate.

Example 7—Glioblastoma Multiforme

Glioblastoma multiforme treatment would involve treating the patient with intramuscular HPV, and then direct injection into a tumor of glioblasotma multiforme.

Example 8—Cervical Cancer

Cervical cancer treatment would involve treating the patient with intramuscular HPV, and can also include direct injection into the cervix.

Example 9—Anal Cancer

Anal cancer treatment would involve treating the patient with intramuscular HPV, and can also include direct injection or topical application to the anus.

Use of other HPV vaccines in treating cancer or tumors in accordance with the methods described herein, are fully contemplated and are within the scope of the invention.

While the present invention has been presented in accordance with several preferred and practical embodiments thereof, it is recognized that departures from the instant disclosure are fully contemplated within the spirit and scope of the invention.

What is claimed is:

1. A method for treating a patient having skin cancer, cancerous tumor, or cancerous lesion, said method comprising administering to the patient, a pharmaceutical composition consisting of:
    a human papillomavirus (HPV) vaccine selected from the group consisting of an HPV quadrivalent recombinant vaccine comprising HPV L1 proteins of HPV types 6, 11, 16 and 18, and an HPV multivalent recombinant vaccine comprising HPV L1 proteins of HPV types 16, 18, 31, 33, 45, 52, and 58;
    a second active pharmaceutical ingredient which is an immune-based therapeutic selected from an Immune Checkpoint Inhibitor and (Chimeric Antigen Receptor (CAR) T-cells;
    and a pharmaceutically acceptable carrier.

2. The method of claim 1 wherein the Immune Checkpoint Inhibitor is selected from the group consisting of a Programed Death 1 inhibitor, a Programed Death Ligand inhibitor, and a Cytotoxic T-lymphocyte-Associated Protein 4 inhibitor.

3. The method of claim 2 wherein the Programed Death 1 inhibitor or Programed Death Ligand inhibitor is Cemiplimab, Atezolizumab, Avelumab, Bavencio, Durvalumab, Imfinzi, Keytruda, Nivolumab, Opdivo, Pembrolizumab, or Tecentriq.

4. The method of claim 1 wherein the CAR T-cells are bispecific antibodies or monoclonal antibodies.

5. The method of claim 4 wherein the bispecific antibodies are Catumaxomab.

6. The method of claim 4 wherein the monoclonal antibodies are Campath, Brutuximab, Vismodigib, Vemurafenib, Dabrfenib, or ecorafenib.

7. The method of claim 1 wherein the vaccine is substantially free of HPV early antigen, E6 or E7.

8. The method of claim 1 wherein the skin cancer, cancerous tumor, or cancerous lesion is substantially reduced in size or eliminated.

9. The method of claim 1 wherein the cancer or cancerous lesion is selected from the group consisting of squamous cell carcinoma, basal cell carcinoma, melanoma, glandular tumor, and adenoma.

10. The method of claim 1, wherein the patient is 27 years of age or older or is previously not immunized with an HPV vaccine.

11. The method of claim 1 wherein the method further comprises: establishing a positive diagnosis of skin cancer, diagnosis of benign or cancerous tumor, or diagnosis of HPV infection, prior to administering the first dose of HPV vaccine.

12. The method of claim 1, said method comprising administering a dose of the pharmaceutic composition directly to a tumor or skin cancer lesion or an area immediately surrounding the tumor, or skin cancer lesion.

13. The method of claim 1 wherein the the pharmaceutic composition is administered by injection.

14. The method of claim 1 wherein the the pharmaceutic composition is administered to the patient in a fixed-dose combination product.

15. The method of claim 1, wherein the patient is administered a second dose of vaccine and immune-based therapeutic at least one month following the first administration, and optionally is administered a third dose of vaccine and immune-based therapeutic at least one month following the second administration.

16. An anticancer pharmaceutical composition consisting of:
an HPV vaccine selected from the group consisting of an HPV quadrivalent recombinant vaccine comprising HPV L1 protein of HPV types 6, 11, 16 and 18, and an HPV multivalent recombinant vaccine comprising HPV L1 protein of HPV types 16, 18, 31, 33, 45, 52, and 58;
a second active pharmaceutical ingredient which is an immune-based therapeutic selected from an Immune Checkpoint Inhibitor and CAR T-cells;
and a pharmaceutically acceptable carrier.

17. The composition of claim 16 wherein the Immune Checkpoint Inhibitor is selected from the group consisting of a Programed Death 1 inhibitor, a Programed Death Ligand inhibitor, and a Cytotoxic T-lymphocyte-Associated Protein 4 inhibitor.

18. The composition of claim 17 wherein the Programed Death 1 inhibitor or Programed Death Ligand inhibitor is Cemiplimab, Atezolizumab, Avelumab, Bavencio, Durvalumab, Imfinzi, Keytruda, Nivolumab, Opdivo, Pembrolizumab, or Tecentriq.

19. The composition of claim 16 wherein the CAR T-cells are bispecific antibodies which is Catumaxomab or monoclonal antibodies Campath, Brutuximab, Vismodigib, Vemurafenib, Dabrfenib, or ecorafenib.

* * * * *